United States Patent [19]

Lai

[11] Patent Number: 5,010,178

[45] Date of Patent: Apr. 23, 1991

[54] PROCESS FOR THE PREPARATION OF MIXED AZONITRILE CARBOXYLIC ACID INITIATORS

[75] Inventor: John T. Lai, Broadview Heights, Ohio

[73] Assignee: The B. F. Goodrich Company, Akron, Ohio

[21] Appl. No.: 456,886

[22] Filed: Dec. 26, 1989

[51] Int. Cl.$^5$ .................... C07C 245/04; C08F 4/04
[52] U.S. Cl. .................... 534/586; 526/218.1; 526/219; 534/838; 534/886; 534/887; 534/587; 534/583
[58] Field of Search ............ 534/838, 886, 887, 586, 534/587, 583; 526/218, 219

[56] References Cited

U.S. PATENT DOCUMENTS 4,039,527  8/1977  Nagaoka et al. .................... 534/838

FOREIGN PATENT DOCUMENTS 740125  3/1970  Belgium ............................ 534/838
226588  9/1968  U.S.S.R. ............................ 534/586

*Primary Examiner*—Floyd D. Higel
*Attorney, Agent, or Firm*—Daniel J. Hudak

[57] ABSTRACT

Disclosed are processes for the preparation of mixed azodinitriles initiators of the formulae

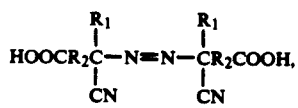

I

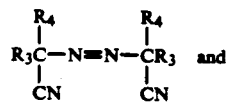

II

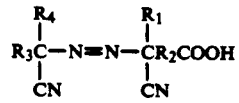

III

These initiators are prepared by reacting a keto acid of the formula

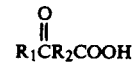

with $M(CN)_x$, a hydrazine source, a ketone of the formula

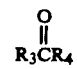

and hydrochloric acid to form

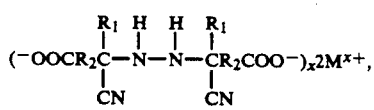

IV

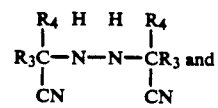

V

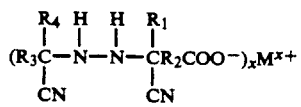

VI

The hydrazo intermediates are reacted with chlorine gas in the presence of acetone solvent to oxidize the mixture of hydrazo intermediates to the mixed azonitrile initiators. $R_1$ is an alkyl group containing from about 1 to about 12 carbon atoms, $R_2$ is non-existent or an alkylene group containing from 1 to about 12 carbon atoms, or a cycloalkylene or alkyl cycloalkylene group containing from about 3 to about 12 carbon atoms, $R_3$ and $R_4$ are alkyl groups containing from 1 to about 12 carbon atoms, or one of $R_3$ and $R_4$ is an alkoxy group containing from 1 to about 4 carbon atoms and M is a metal comprising lithium, sodium, potassium, magnesium, or calcium.

23 Claims, No Drawings

PROCESS FOR THE PREPARATION OF MIXED AZONITRILE CARBOXYLIC ACID INITIATORS

FIELD OF THE INVENTION

The present invention relates to an improved process for the preparation of mixed azonitrile initiators. There is a two-fold purpose for making mixed azonitrile initiators: (1) simple ketones such as acetone are less expensive than keto acids such as levulinic acid and (2) some applications do not need high viscosity; that is, a non-carboxylic acid azonitrile initiator is less viscous than a carboxylic acid azonitrile initiator.

The various important properties of mixed azonitrile initiators are physical state, solubility, volatility, toxicity, thermal stability and initiator efficiency and these properties are dependent upon the nature of the end groups carboxyl and alkyl. The thermal stability of mixed azonitrile initiators is intermediate between the stabilities of symmetrical azonitrile initiators HOOCR-N=N-RCOOH or R—N=N—R and the unsymmetrical azonitrile initiator HOOCR—N=N—R. Many of the mixed azonitrile initiators have unique thermal and initiator properties which cannot be duplicated by the purely symmetrical or purely unsymmetrical azonitrile initiators. Mixtures of azonitrile initiators have unique thermal and initiator properties that may extend over a wide temperature range depending upon the end groups.

BACKGROUND

It is known in the art to prepare diazocyano acids using a keto acid or a sodium salt of a keto acid as the starting material.

U.S. Pat. Nos. 4,684,717 and 4,684,718 (Ashitaka et al, Aug. 4, 1987) provide a process for the preparation of diazocyano acid, which comprises reacting a keto acid or its sodium salt with a cyanogen compound such as sodium cyanide or hydrogen cyanide and a hydrazine in water to form a concentrated aqueous solution of a hydrazo compound, adding acetone and/or water to the concentrated aqueous solution to form a solution of the hydrazo compound, adding chlorine gas to the solution to oxidize the hydrazo compound and form a diazocyano acid, and separating the diazocyano acid from the obtained reaction mixture.

U.S. Pat. No. 4,831,096 (MacLeay, May 16, 1989) relates to mixtures of azoalkanes of varying thermal stabilities at least one of which is an unsymmetrical azoalkane (R—N=N—R'). These unsymmetrical azoalkanes are prepared by reacting four equivalents of a mixture of two or more primary alkyl, cycloalkyl or aralkyl amines with one equivalent of sulfuryl chloride in an inert solvent and oxidizing the resulting mixture of sulfamide products with basic bleach. The unsymmetrical azoalkanes can be separate from the symmetrical azoalkanes by a variety of conventional techniques. The azoalkane mixtures are polymerization initiators for vinyl monomers and curing agents for unsaturated polyester resins.

SUMMARY OF THE INVENTION

This invention relates to a process for preparing mixed azonitrile initiators of the formulae:

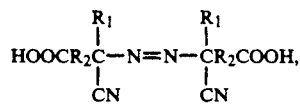

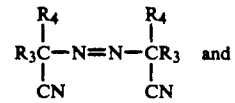

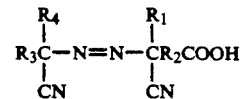

In the above formulae, $R_1$ is an alkyl group containing from 1 to about 12 carbon atoms, $R_2$ is non-existent or an alkylene group containing from 1 to about 12 carbon atoms. $R_2$ may also be a cycloalkylene or alkyl cycloalkylene group containing from 3 to about 12 carbon atoms. $R_3$ and $R_4$ are alkyl groups containing from 1 to about 12 carbon atoms. One of $R_3$ and $R_4$ may be an alkoxy group of from 1 to about 4 carbon atoms.

DETAILED DESCRIPTION OF THE INVENTION

Mixed azonitrile initiators prepared by the process of this invention are: less expensive due to the utilization of acetone as a ketone, have a lower viscosity than diazocyano acids since the mixed azonitrile initiator has terminal end groups of either carboxyl or alkyl and are prepared in an acetone solution with said acetone solution being used directly for the polymerization without isolation of the mixed azonitrile initiator.

The various important properties of mixed azonitrile initiators are physical state, solubility, volatility, toxicity, thermal stability and initiator efficiency and these properties are dependent upon the nature of the end groups carboxyl and alkyl. The thermal stability of mixed azonitrile initiators is intermediate between the stabilities of symmetrical azonitrile initiators HOOCR—N=N—RCOOH or R—N=N—R and the unsymmetrical azonitrile initiator HOOCR—N=N—R. Many of the mixed azonitrile initiators have unique thermal and initiator properties which cannot be duplicated by the symmetrical or unsymmetrical azonitrile initiators. Mixtures of unsymmetrical and symmetrical or unsymmetrical azonitrile initiators have unique thermal and initiator properties that may extend over a wide temperature range depending upon the end groups and the ratio of symmetrical:unsymmetrical azonitrile initiators.

The azonitrile initiators have the chemical moiety

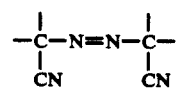

and the —N=N— moiety is indicative of an azo compound. In the practice of this invention, the azo moiety is generated from a hydrazo moiety

by the oxidative effect of chlorine gas. This invention is directed to three different processes for the preparation of the hydrazo moiety.

The three processes to prepare the hydrazo moiety all utilize a keto acid, a cyanohydrin, a metal cyanide, and a hydrazine source. The cyanohydrin may be used as a starting material or it may be formed in situ.

The Keto Acid

The keto acids having utility in this invention are of the general formula

$R_1$ is an alkyl group containing from 1 to about 12 carbon atoms, preferably from 1 to about 6 carbon atoms and most preferably from 1 to about 3 carbon atoms. Such groups are known to those skilled in the art. Examples include methyl, ethyl, propyl, isopropyl, butyl, isobutyl and t-butyl.

$R_2$ is an alkylene or cycloalkylene group containing from 1 to about 12 carbon atoms and preferably 1 to about 6 carbon atoms. When $R_2$ is not cyclic $R_2$ most preferably contains from 1 to about 4 carbon atoms. When $R_2$ is cyclic it most preferably contains from about 3 to about 6 carbon atoms. Some examples of $R_2$ cyclic alkylenes are

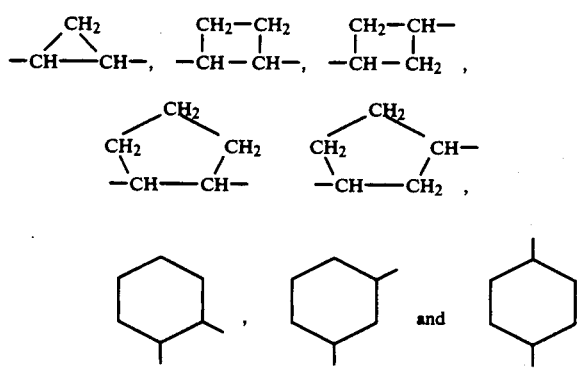

When $R_2$ is not cyclic, examples are methylene, ethylene, propylene, butylene, as well as any branching thereof. The following table lists a few of the many keto acids having utility in this invention. This list is merely illustrative and is not meant to be all-inclusive. A preferred keto acid is levulinic acid.

TABLE I

| Keto Acids | | |
|---|---|---|
| $R_1$ | $R_2$ | Name |
| $CH_3$ | a direct bond | pyruvic acid |
| $CH_3$ | $CH_2$ | 3-oxobutanoic acid |
| $CH_3$ | $CH_2CH_2$ | levulinic acid |
| $CH_3$ | $CH_2CH_2CH_2$ | 5-oxohexanoic acid |
| $CH_3$ | $CH_2CH_2CH_2CH_2$ | 6-oxoheptanoic acid |
| $CH_3$ | $CH_2CH_2CH_2CH_2CH_2$ | 7-oxooctanoic acid |
| $CH_3CH_2$ | a direct bond | 2-oxobutanoic acid |
| $CH_3CH_2$ | $CH_2$ | 3-oxopentanoic acid |
| $CH_3CH_2$ | $CH_2CH_2$ | 4-oxohexanoic acid |
| $CH_3CH_2$ | $CH_2CH_2CH_2$ | 5-oxoheptanoic acid |
| $CH_3CH_2CH_2$ | $CH_2CH_2$ | 4-oxoheptanoic acid |
| $CH_3$ | $CH_2CH$<br>\|<br>$CH_3$ | 2-methyllevulinic acid |

The Cyanohydrin

Cyanohydrins having utility in this invention are of the general formula

$R_3$ and $R_4$ are alkyl groups independently containing from 1 to about 12 carbon atoms, preferably from 1 to about 6 carbon atoms and most preferably from 1 to about 4 carbon atoms. The alkyl groups may be branched or straight chained. One of the groups $R_3$ or $R_4$ may also be an alkoxy group containing from i to about 4 carbon atoms. A preferred cyanohydrin is acetone cyanohydrin. The cyanohydrin may be formed in situ by the reaction of $CN^-$ on the carbonyl moiety, $>C=O$ of a ketone

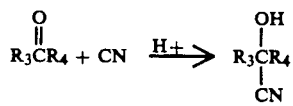

A preferred ketone is acetone where $R_3$ and $R_4$ are methyl groups.

The Metal Cyanide

One mole of the keto acid is reacted with from about 1 to about 2 equivalents of a metal cyanide of the formula $M(CN)_x$ and a catalytic amount of hydrochloric acid wherein the metal M comprises lithium, sodium, potassium, magnesium, or calcium and x is the valence of M. The reaction of the keto acid with $M(CN)_x$ to form a cyanohydrin metal carboxylate is an addition reaction with no by-products formed. A preferred metal cyanide is sodium cyanide.

Hydrazine Source

As examples of the hydrazine source, there can be mentioned both hydrazine and hydrazine hydrate. Preferred is hydrazine hydrate.

Depending upon the order of addition, at least three different processes exist for the formation of the hydrazo moiety —NH—NH—.

In one process, a keto acid is reacted with $M(CN)_x$ in the presence of a slight amount of concentrated hydrochloric acid to form a cyanohydrin metal carboxylate.

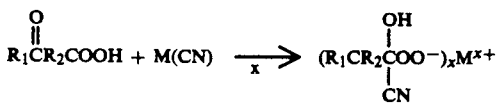

After formation of the cyanohydrin metal carboxylate, a cyanohydrin is added followed by the hydrazine to give rise to the three hydrazo formulae:

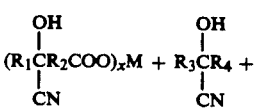

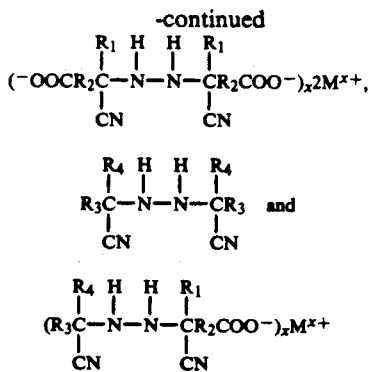

For every mole of keto acid used, 1 to 2, preferably 1 to 1.5 and most preferably 1 to 1.1 equivalents of $M(CN)_x$ is used; 0.1 to 10.0, preferably 0.5 to 2.0 and most preferably 0.8 to 1.5 moles of cyanohydrin is employed, and 0.4 to 0.75, preferably 0.4 to 0.6 and most preferably 0.45 to 0.55 moles of a hydrazine source is used.

Acetone is added to the mixed hydrazo intermediates at a molar ratio of cyanohydrin plus keto acid:acetone of from about 1.5 to about 1:30, preferably from about 1:7 to about 1:12 and most preferably from about 1:8 to about 1:10 moles. After the acetone is added, chlorine gas is bubbled into the hydrazo intermediates to oxidize the hydrazo intermediates to azo compounds. HCl is generated which reacts with the metal carboxylate to give the free carboxylic acid thus forming the mixed azonitrile initiators of Formulae I, II and III.

In another process, a keto acid, ketone, metal cyanide and catalytic amount of hydrochloric acid are reacted together and the cyanohydrin is formed in situ from the ketone.

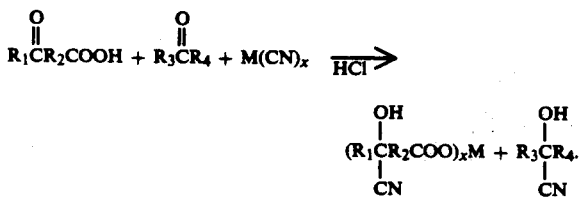

The products formed are then reacted with hydrazine hydrate to form the mixed hydrazo intermediates. Acetone is added and the mixed hydrazo intermediates are further reacted with chlorine gas as per the previous process to obtained the mixed azonitrile initiators of formulae I, II, and III. For every mole of keto acid used, from about 0.1 to about 10, preferably from about 0.5 to about 2.0 and most preferably from about 0.8 to about 1.5 moles of ketone is employed. The ratios of the other various reactants are as per the previous process.

In still another process, the keto acid is added to an aqueous solution of a metal cyanide and hydrazine hydrate followed by a ketone and HCl gas.

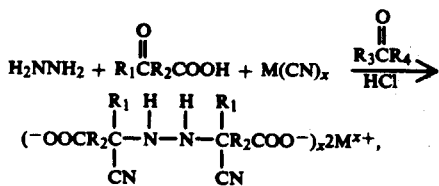

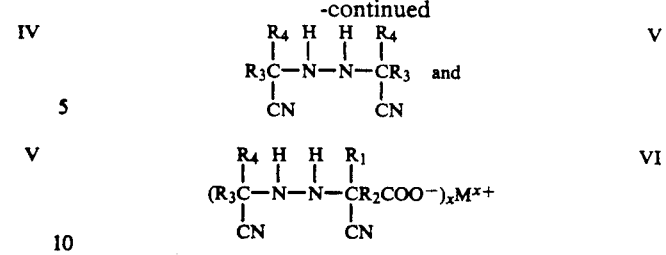

Acetone, as a solvent, is added and the mixed hydrazo intermediates are further reacted with chlorine gas as per the previous process to obtained the mixed azonitrile initiators of formulae I, II, and III. The ratios of the various reactants are as per the previous processes.

The following examples are illustrative of the preparation of mixed azonitrile initiators. Unless otherwise indicated, all parts and percentages are by weight.

EXAMPLE 1

Added to a one liter three-neck round bottom flask with addition funnel thermometer and mechanical stirrer was 20.3 parts (0.41 moles) NaCN in 40 parts water. Stirring was begun and 46.4 parts (0.40 moles) levulinic acid in 40 parts water was added. About 2.8 parts concentrated HCl was added followed by 10 parts water. An additional 20.3 parts NaCN followed by 10 parts rinse water for the funnel was added and a temperature maintained at between 20°-30° C. for 30 minutes. At 20° to 30° C., 34.7 parts (0.4 moles) acetone cyanohydrin was added followed by 5 parts water. About 10 to 15 minutes later at less than 30° C., 23 parts (0.39 moles) hydrazine hydrate was added and the funnel was rinsed with 20 parts water. After 15 minutes, the pH was adjusted to 6 with the addition of hydrochloric acid and the contents were heated to 35° C. and held there for two hours. The contents were cooled to 5°-10° C. and 416 parts acetone were added. The formed mixed hydrazo intermediates were then oxidized by bubbling in 30.2 parts chlorine. The pH prior to chlorine addition was 7.56 and 3.86 at the end of the addition. The pH was kept between 3-7.56 by adding 34 parts of 50 percent aqueous sodium hydroxide during the chlorine addition. The maximum temperature during oxidation was 15° C. Two layers were formed and separated. The upper acetone solution was concentrated and vacuum dried to obtain 137.3 parts solid. Nitrogen analysis indicated that this solid contained 58.6 percent azodinitriles which related to 90.6 percent yield. Note: The upper acetone solution can be used directly for polymerization. The purpose of the work-up was to determine the percent yield.

EXAMPLE 2

Added to a one liter three-neck round bottom flask with addition funnel thermometer and mechanical stirrer were 46.4 parts (0.4 moles) levulinic acid, 23.2 parts (0.4 moles) acetone and 40 parts water. The temperature was lowered to 5°-10° C. and 5.6 parts concentrated HCl was added followed by 20 parts water. About 40.5 parts (0.83 moles) NaCN in 80 parts water was added dropwise at between 5°-10° C. and the funnel was rinsed with 20 parts water. At 10° C. 40.6 parts concentrated HCl was added and the contents were stirred at 5°-10° C. for 20 minutes. The contents were then heated to 30° C. and 23 parts (0.39 moles) hydrazine hydrate was charged followed by rinsing the funnel with 10 parts water. The contents were stirred for 15 minutes and the pH was 6. The contents were kept at 30°-35° C. for an additional one hour and then the temperature was lowered to 5°-10° C. About 416 parts acetone was charged and 30 parts chlorine gas was charged below the surface over 1 hour and 40 minutes. During the chlorination the pH went to 0 and was adjusted to about 6 using 26.5 parts of 50 percent aqueous sodium hydroxide solution. After the oxidation was complete, the pH was adjusted to 3.74 with 6.5 parts 50 percent aqueous sodium hydroxide solution. Two layers were formed and separated. The upper acetone solution was concentrated and vacuum dried to obtain 145 parts white semi-solid. Under nitrogen analysis, a sample of the product was found to contain 45.6 percent azodinitriles which related to a 74.5 percent yield.

EXAMPLE 3

Added to a one liter three-neck round bottom flask with addition funnel, thermometer, and mechanical stirrer were 58.5 parts (0.5 moles) levulinic acid, 17.4 parts (0.3 moles) acetone and 80 parts water. Stirring was begun and 5.6 parts concentrated HCl was added and the funnel was rinsed with 20 parts water. At between 20°-30° C., 40.5 parts (0.83 moles) NaCN in 80 parts water was added dropwise and the funnel was rinsed with 20 parts water. Stirring was continued for 20 minutes at which time 23 parts (0.39 moles) hydrazine hydrate was added at 30° C. The funnel was rinsed with 20 parts water. Stirring was continued for an additional 15 minutes and the pH was adjusted to 6 with about 30 parts concentrated HCl. The contents were stirred for 1.5 hours at 35° C. and the temperature was lowered to 5°-10° C. About 416 parts acetone was added dropwise at 5°-10° C. About 29.9 parts chlorine gas was blown below the surface over 1.5 hours with the temperature between 5°-10° C. The pH was adjusted to 4 by the addition of concentrated hydrochloric acid. Two layers were formed and separated. The upper acetone solution was washed with 50 ml saturated sodium chloride solution and an extra 19 ml aqueous layer was obtained. The acetone layer was concentrated and vacuum dried at below 35° C. to obtain 110 parts semi-solid. Under nitrogen analysis, a sample of the product was found to contain 52.3 percent mixed azodinitriles which related to a 75.1 percent yield.

EXAMPLE 4

Added to a one liter three-neck round bottom flask with addition funnel, thermometer, and mechanical stirrer were 40.5 parts (0.83 moles) NaCN in 80 parts water. The contents were cooled to 20° C. and 23 parts (0.39 moles) hydrazine hydrate were added followed by 40.6 parts (0.4 moles) levulinic acid and the funnel rinsed each time with 5 parts water. At 20° C., 23.3 parts (0.4 moles) acetone and 41.5 parts concentrated HCl were both added dropwise. About 20 minutes after addition of HCl, the pH was about 7. The contents were heated to 35° C. and held there 1.5 hours and then cooled to 5°-10° C. About 416 parts acetone were added dropwise and chlorine gas was blown below the surface to oxidize the hydrazo intermediate. The pH dropped to 0.7 and was adjusted to 3.1 using 31.6 parts 50 percent aqueous sodium hydroxide solution. Two layers were formed and separated. The upper acetone solution was concentrated and vacuum dried to obtain 138.7 parts crude semi-solid. Nitrogen analysis showed the sample to contain 56.5 percent azodinitriles which related to an 88 percent yield.

While in accordance with the Patent Statutes, the best mode and preferred embodiment has been set forth, the scope of the invention is not limited thereto, but rather by the scope of the attached claims.

What is claimed is:

1. A process for the preparation of mixed azonitrile initiators, comprising; forming

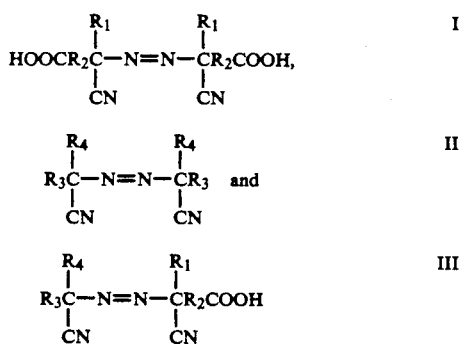

by reacting a keto acid of the formula

with $M(CN)_x$ and a catalytic amount of hydrochloric acid to form a cyanohydrin metal carboxylate of the formula

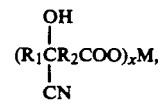

adding to the cyanohydrin metal carboxylate a cyanohydrin of the formula

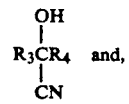

reacting the mixture with a hydrazine source to obtain a mixture of hydrazo intermediates of the formulae

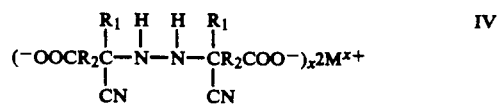

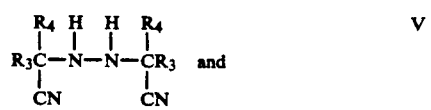

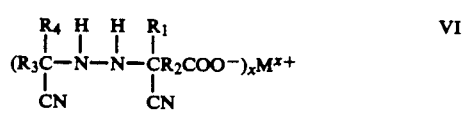

and reacting said mixture of hydrazo intermediates with chlorine gas in the presence of acetone solvent to oxidize the mixture of hydrazo intermediates and form the mixed azonitrile initiators wherein $R_1$ is an alkyl containing from about 1 to about 12 carbon atoms, $R_2$ is a direct bond or an alkylene containing from 1 to about 12 carbon atoms, or a cycloalkylene or alkyl cycloalkylene containing from about 3 to about 12 carbon atoms, $R_3$ and $R_4$, independently, are alkyls containing from 1 to about 12 carbon atoms, or one of $R_3$ and $R_4$ is an alkoxy containing from 1 to about 4 carbon atoms, and M is a metal selected from the class consisting of lithium, sodium, potassium, magnesium, or calcium.

2. The process of claim 1 wherein the equivalents of metal cyanide:moles of keto acid is from about 1-2:1.

3. The process of claim 2 wherein the moles of hydrazine source:moles of keto acid is from about 0.4-0.75:1.

4. The process of claim 3 wherein the molar ratio of cyanohydrin:keto acid is from about 0.1-10.0:1.

5. The process of claim 4 wherein the molar ratio of cyanohydrin pulse keto acid:acetone in the hydrazo intermediate is from about 1:5-30.

6. The process of claim 5 wherein the equivalents of metal cyanide:moles of keto acid is from about 1-1.1:1.

7. The process of claim 6 wherein the moles of hydrazine source:moles of keto acid is from about 0.45-0.55:1.

8. The process of claim 7 wherein the hydrazine source is hydrazine hydrate and M is sodium.

9. The process of claim 8 wherein the molar ratio of cyanohydrin:keto acid is from about 0.8-1.5:1.

10. The process of claim 9 wherein the molar ratio of cyanohydrin plus keto acid:acetone in the hydrazo intermediate is from about 1:8-10, wherein $R_1$ contains from 1 to about 6 carbon atoms, and $R_2$ is an alkylene containing from 1 to about 6 carbon atoms.

11. The process of claim 10 wherein the keto acid is levulinic acid.

12. A process for the preparation of mixed azonitrile initiators, comprising: forming

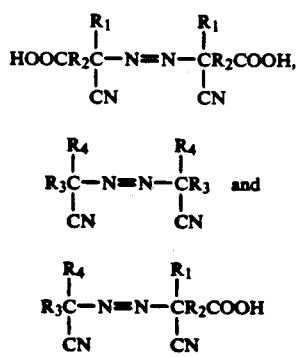

by reacting a keto acid of the formula

with $M(CN)_x$ and a ketone of the formula

in the presence of hydrochloric acid to obtain a mixture of cyanohydrins of the formulae

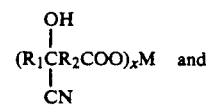

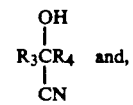

reacting the cyanohydrin mixture with a hydrazine source to obtain a mixture of hydrazo intermediates of the formulae

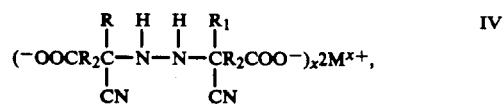

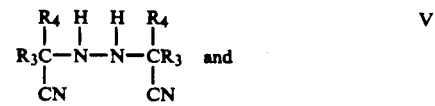

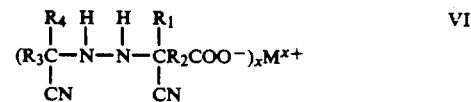

and,
reacting said mixture of hydrazo intermediates with chlorine gas in the presence of acetone solvent to oxidize the mixture of hydrazo intermediates to form the mixed azonitrile initiators wherein $R_1$ is an alkyl containing from about 1 to about 12 carbon atoms, $R_2$ is a direct bond or an alkylene containing from 1 to about 12 carbon atoms, or a cycloalkylene or alkyl cycloalkylene containing from about 3 to about 12 carbon atoms, $R_3$ and $R_4$ independently are alkyl containing from 1 to about 12 carbon atoms, or one of $R_3$ and $R_4$ is an alkoxy containing from 1 to about 4 carbon atoms and M is a metal selected from the class consisting of lithium, sodium, potassium, magnesium, or calcium.

13. The process of claim 12 wherein the equivalents of metal cyanide:moles of keto acid is from about 1-1.1:1.

14. The process of claim 13 wherein the moles of hydrazine source:moles of keto acid is from about 0.45-0.55:1.

15. The process of claim 14 wherein the molar ratio of ketone:keto acid is from about 0.8-1.5:1.

16. The process of claim 15 wherein the molar ratio of cyanohydrins:acetone in the hydrazo intermediate is from about 1:8-10.

17. The process of claim 16 wherein the hydrazine source is hydrizine hydrate, M is sodium and the keto acid is levulinic acid.

18. A process for the preparation of mixed azonitrile initiators comprising; forming

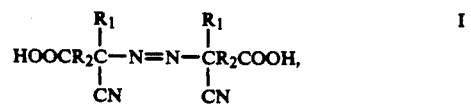

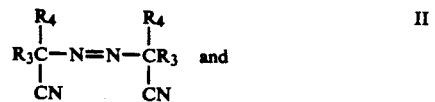

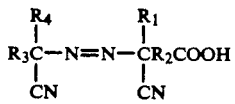   III by reacting a keto acid of the formula

with $M(CN)_x$ and a hydrazine source in the presence of a ketone of the formula

to obtain a mixture of hydrazo intermediates of the formulae

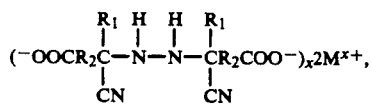   IV

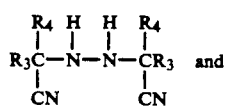   V

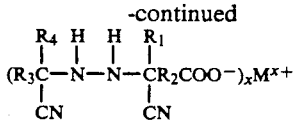   VI and reacting said mixture of hydrazo intermediates with chlorine gas in the presence of acetone solvent to oxidize the mixture of hydrazo intermediates to form the mixed azonitrile initiators wherein $R_1$ is an alkyl containing from about 1 to about 12 carbon atoms, $R_2$ is a direct bond or an alkylene containing from 1 to about 12 carbon atoms, or a cycloakylene or alkyl cycloalkylene containing from about 3 to about 12 carbon atoms, $R_3$ and $R_4$ independently are alkyl containing from 1 to about 12 carbon atoms, or one of $R_3$ and $R_4$ is an alkoxy containing from 1 to about 4 carbon atoms, and M is a metal selected from the class consisting of lithium, sodium, potassium, magnesium, or calcium.

19. The process of claim 18 wherein the equivalents of metal cyanide:moles of keto acid is from about 1-1.1:1.

20. The process of claim 19 wherein the moles of hydrazine source:moles of keto acid is from about 0.45-0.55:1.

21. The process of claim 20 wherein the hydrazine source is hydrazine hydrate and M is sodium.

22. The process of claim 21 wherein the molar ratio of ketone:keto acid is from about 0.8-1.5:1.

23. The process of claim 22 wherein the molar ratio of cyanohydrins:acetone in the hydrazo intermediate is from about 1:8-10 and the keto acid is levulinic acid.

* * * * *